(12) United States Patent
Zech et al.

(10) Patent No.: US 7,700,712 B2
(45) Date of Patent: Apr. 20, 2010

(54) ALLYLSILANE CONTAINING COMPOSITION

(75) Inventors: Joachim W. Zech, Kaufering (DE); Henning Hoffmann, Windach (DE); Peter Bissinger, Diessen (DE); Wolf Steiger, Geretsried (DE)

(73) Assignee: 3M ESPE AG, Seefeld (DE)

(*) Notice: Subject to any disclaimer, the term of this patent is extended or adjusted under 35 U.S.C. 154(b) by 677 days.

(21) Appl. No.: 10/570,415

(22) PCT Filed: Sep. 3, 2004

(86) PCT No.: PCT/EP2004/009809

§ 371 (c)(1),
(2), (4) Date: Mar. 2, 2006

(87) PCT Pub. No.: WO2005/023934

PCT Pub. Date: Mar. 17, 2005

(65) Prior Publication Data

US 2007/0004858 A1  Jan. 4, 2007

(30) Foreign Application Priority Data

Sep. 4, 2003 (EP) .................. 03020055

(51) Int. Cl.
*C08G 77/20* (2006.01)
(52) U.S. Cl. .......................... 528/32; 528/31
(58) Field of Classification Search .............. 528/31, 528/32
See application file for complete search history.

(56) References Cited

U.S. PATENT DOCUMENTS

| | | | |
|---|---|---|---|
| 3,159,662 A | 12/1964 | Ashby | |
| 3,220,972 A | 11/1965 | Lamoreaux | |
| 3,410,886 A | 11/1968 | Joy | |
| 3,715,334 A | 2/1973 | Karstedt | |
| 3,775,352 A | 11/1973 | Leonard | |
| 3,814,730 A | 6/1974 | Karstedt | |
| 3,933,880 A | 1/1976 | Bergstrom et al. | |
| 4,273,902 A | 6/1981 | Tomioka et al. | |
| 4,742,103 A * | 5/1988 | Morita et al. | ............... 524/174 |
| 4,957,667 A | 9/1990 | Hamer | |
| 5,286,105 A | 2/1994 | Herold et al. | |
| 5,684,060 A | 11/1997 | Konings | |

FOREIGN PATENT DOCUMENTS

| | | |
|---|---|---|
| EP | 0268347 B2 | 5/1988 |
| EP | 0492413 B1 | 7/1992 |
| EP | 0599532 A | 6/1994 |
| WO | WO 97/37632 | 10/1997 |

OTHER PUBLICATIONS

DIN 50125.
DIN 53018-1.
DIN 53505.
J. Burkhardt, Chemie und Technologie der Polysiloxane in "Silikone, Chemie und Technologie", Vulkan Verlag, Essen, 1989, pp. 23-37.
W. Noll, "Chemie und Technologie der Silikone", Verlag Chemie Weinheim 2. edition 1964, pp. 162-206.
"Silicones", Kirk-Othmer Encyclopedia of Chemical tecnology, 3rd Ed., 20, 922-962 (1982).
International Preliminary Report on Patentability and Written Opinion for PCT/EP2004/009809; 6 pgs.

\* cited by examiner

*Primary Examiner*—Kuo-Liang Peng (57) ABSTRACT

The invention provides a method to reduce evolution of hydrogen gas especially during pouring gypsum models from addition cured silicones. In this respect the invention relates to an addition curable silicone composition, comprising an addition-curable siloxane compound, a siloxane crosslinker, a catalyst and an unsaturated silane compound with at least one methylene group directly attached to the unsaturation in an amount effective to reduce the amount of hydrogen gas evolved in the reaction of said composition.

25 Claims, 2 Drawing Sheets

ALLYLSILANE CONTAINING COMPOSITION

This application is a national stage filing under 35 U.S.C. 371 of PCT/EP2004/009809, filed Sep. 3, 2004, which claims priority to European Application No. 03020055.4, filed Sep. 4, 2003, the disclosure of which is incorporated by reference in its entirety herein.

The invention provides for an alternative and new way to avoid and/or reduce evolution of hydrogen gas during pouring gypsum models from addition cured silicones, especially VPS impression materials by addition of small amounts of certain unsaturated silane compounds into the VPS formulation.

Many addition-curable compounds, particularly addition-curable silicone dental compositions, release hydrogen gas as a by-product of the reaction of an organo poly siloxane with vinyl groups and an organo hydrogen poly siloxane in the presence of a catalyst. The hydrogen gas evolution may cause undesirable imperfections or pits in a material subsequently applied to or poured into the dental impression (i.e., negative model) to form a positive model. This may result in the formation of an article which is unacceptable or, in the case of a dental device, does not fit properly.

The evolution of hydrogen gas can be a problem because the step after making an impression is forming a positive model by filling the impression with a material such as plaster of Paris (i.e., gypsum), wax or epoxy. If hydrogen gas is evolving, bubbles form at the surface of the impression material which result in pits in the subsequently poured and hardened gypsum.

Alternatively, a palladium compound may be applied to at least a portion of the surface of the impression or incorporated in the impression material or in the positive model material prior to pouring the model material into the impression.

In this respect U.S. Pat. No. 4,273,902 describes the use of finely divided palladium metal powder, palladium alloys or palladium metal as hydrogen scavengers in addition-cure silicone impression material formulations.

U.S. Pat. No. 4,957,667 describes the use of finely divided palladium applied over at least a portion of the negative impression material before pouring the settable positive impression material or admixture of finely divided palladium with the positive impression material prior to pouring.

EP 0 268 347 B2 describes the use of platinum black instead of palladium as a hydrogen scavenger in VPS impression materials which can be made hydrophilic by the addition of surfactants.

WO 97/37632 A1 relates to the use of a palladium compound in an amount effective to reduce the amount of hydrogen gas evolved in the reaction of a VPS composition. A significantly reduced amount of palladium is needed by an in-situ formation of colloidal palladium during the setting reaction.

The hydrogen scavengers used in these systems are based on elemental palladium or platinum and make use of the huge capacity of these noble metals to absorb gaseous hydrogen under environmental conditions. These noble metals can be added to the formulations either as metals or as palladium compounds which can be reduced in the system which leads to the formation of finely divided palladium.

All these solutions show several disadvantages. Usually in two component VPS formulations the noble metals cannot be added to the base paste but to the catalyst paste only due to inducement of a slow curing reaction in the base paste. However, in the catalyst paste the amount of those noble metals is limited due to reduction of the shelf life of the Karstedt platinum catalyst which is needed for a quick setting of VPS impression materials.

Because of this limitations the amount of hydrogen which can be absorbed is limited and in some cases could be not sufficient.

In addition to that there are also issues with respect to the price of such noble metal systems and to the color of the products because of the black or grayish appearance of the noble metal colloids. Therefore, there is a strong need for an alternative way to reduce the amount of hydrogen in addition cured silicones, especially VPS impression materials.

It is thus an object of the invention to alleviate one or more of the problems mentioned above.

It is also an object of the invention to provide a composition with improved properties, especially a composition which enables one to produce a positive model with less imperfections or pits from an impression, preferably a dental impression.

It is another object of the present invention to provide a composition with an improved capability in reducing hydrogen released from addition curable silicone dental impression material compositions.

It has been found that one or more of the above mentioned objects can be achieved by providing a composition as described in the text and claims below.

The invention provides a novel solution to providing a substantially pit-free positive model of a curable addition cure silicone composition.

In this respect the invention relates to an addition curable silicone composition, comprising
   a) an addition-curable siloxane compound (A),
   b) a siloxane crosslinker (B),
   c) a platinum containing catalyst (C),
   d) an unsaturated silane compound with at least one methylene group directly attached to the unsaturation (D), preferably only one unsaturated group, in an amount effective to reduce the amount of hydrogen gas evolved in the reaction of the composition,
   e) optionally an inhibitor (E),
   f) optionally a filler (F),
   g) optionally additives (G) selected from modifiers, fillers, dyes, pigments, thixotropic agents, flow improvers, polymeric thickeners, surfactants, odorous substances, diluting agent(s) and/or flavourings.
      wherein the composition does not contain an acetylenic alcohol containing at least 6 carbon atoms.

Addition of an acetylenic alcohol might inhibit cure of the composition under ambient conditions as described in EP 0 599 532 A2.

The term unsaturated silane compound with at least one methylene group directly attached to the unsaturation (D) according to the invention comprises every silane capable of effectively reducing hydrogen released as a by-product of the reaction of an organo polysiloxane with vinyl groups and an organo hydrogen polysiloxane in the presence of a catalyst.

The amount of unsaturated silane compound should be sufficient to reduce the evolution of hydrogen gas released from an addition-curable composition in which it has been incorporated. This can be determined by gas chromatography ("GC") in a Hydrogen Gas Evolution Value test or by counting the bubbles caused by hydrogen gas evolution on the surface of a positive mold.

The measurement is usually done at standard temperature and pressure ("STP", i.e. 25° C. and 1023 hPas). Hydrogen standards were prepared over the range to be tested. The first standard was prepared by injecting 0.25 ml of hydrogen gas into a 856.5 ml gas sampling bulb. The bulb was shaken and two injections of 0.5 ml were made within two minutes of each other. A total of four standards were prepared using 0.25, 0.50, 1.00 and 1.50 ml of hydrogen gas and the standard curve was calculated. All samples were analyzed by GC (Hewlet Packard Model 5890, Series 11 with thermoconductivity detector and 333396 Series 11 integrator). The GC was equipped with a 1.8 meter long and 3.2 millimeter diameter stainless steel column packed with Type 5A molecular sieve (60/80 mesh size, Applied Science, Deerfield, Ill. The injector port temperature was set at 120° C., the column oven and program isothermal at 45° C. and the detector at 200° C., Nitrogen was used as the carrier gas at flow rates of 20 ml-per minute on tile sample side and 30 ml per minute on the reference side, Impression material (10.0 g) of each run was extruded through a static mixer onto a tared square of glassine weighing paper. The sample was weighed to the nearest tenth of a gram and immediately placed into a calibrated 1030 ml round-bottom flask equipped with a stopcock and rubber septum. At a specified time, two 0.5 ml, samples of gas were removed from the flask using a 0.5 ml M Precision gas-tight syringe (Precision Sampling Corp., Baton Rouge, La.) and 1 injected into the sample side of the GC within 2 minutes of each other.

Preferably the amount of hydrogen evolved in 2 hours per 10.0 g of impression material is less than about 0.6 ml, or less than about 0.4 ml or less than about 0.2 ml.

The unsaturated silane compound can be present in an amount of up to about 10% by weight, or up to about 5% by weight, or up to about 1% by weight with respect to the cured composition.

The amount of the unsaturated silane compound can be as low as about 0.001% by weight, or about 0.05% by weight, or about 0.1% by weight with respect to the cured composition.

The unsaturated silane compound can have a viscosity below or up to about 200 mPas, or below or up to about 100 mPas, or below or up to about 50 mPas, at 23° C.

The molecular weight of the unsaturated silane compound can be below or up to about 1000 gmol$^{-1}$, or below or up to about 500 gmol$^{-1}$.

The unsaturated silane compound can be mono functional.

The term mono functional according to the invention is defined as a compound with only one unsaturated group, preferably not comprising groups like carbonyl, ester, sulfur, phosphor and/or amino. The mono functional group is preferably not in α-position to a silicon atom and is preferably not adjacent to a hetero double bond.

The unsaturated silane compound has preferably the following structure:

$$R^2R^3C=CR^1\text{-}A\text{-}SiR_3 \qquad (I)$$

wherein

R can be a monovalent alkyl (linear or branched or cycloalkyl) $C_1$-$C_{22}$, aryl $C_6$-$C_{12}$, alkoxy (linear or branched or cycloalkoxy) $C_1$-$C_{22}$, aryloxy $C_6$-$C_{12}$, O—SiR$^4{}_3$ or H (The residue R may include heteroatoms like O, Cl, Br, F or I. The residues R can be different or equal and are preferably selected from Methyl, Ethyl, Propyl, Isopropyl, Butyl, Isobutyl, sec.-Butyl, tert.-Butyl, Pentyl, Hexyl, Heptyl, Octyl, 2-Ethylhexyl, Nonyl, Decycl, Undecyl, Dodecyl, Tetradecyl, Hexadecyl, Octadecyl Phenyl, Tolyl, Cyclohexyl, Trimethylsiloxy, Triethylsiloxy, tert.-Butyldimethylsiloxy, Methoxy, Ethoxy, Isopropoxy, Butoxy, 3,5,7,9,11,13,15-Heptacyclopentyl-pentacyclo[9.5.1$^{3,9}$1$^{5,15}$.1$^{7,13}$]octasiloxan-1-yl, 3,5,7,9,11,13,15-Hepta-isopropyl-pentacyclo[9.5.1$^{3,9}$1$^{5,15}$.1$^{7,13}$] octasiloxan-1-yl), R$^1$, R$^2$, R$^3$ can be equal or different and comprise hydrogen or monovalent alkyl (linear or branched or cycloalkyl) $C_1$-$C_{22}$, aryl $C_6$-$C_{12}$ (R$^1$ and R$^2$ or R$^3$ can also combine to a cyclic structure. The residues R$^1$, R$^2$ and R$^3$ may include heteroatoms like O, Cl, Br, F or I. Preferred for R$^1$, R$^2$ and R$^3$ is H.), R$^4$ can be monovalent alkyl (linear or branched or cycloalkyl) $C_1$-$C_{22}$, aryl $C_6$-$C_{12}$, wherein two or three of the residues R$^4$ in O—SiR$^4{}_3$ can combine to a cyclic or polycyclic structure like a cyclosiloxane or a polycyclic siloxane structure, A is a divalent linear, branched or cyclic hydrocarbon group $C_1$-$C_{12}$, optionally comprising an aromatic moiety, with at least one methylene group directly attached to the unsaturation, optionally including O-Atoms (A is preferably methylene, ethylene, propylene, butylene, hexylene, octylene, nonylene or decyclene).

The unsaturated silane compound comprises preferably the structural element preferably the structural element H$_2$C=CH—CH$_2$— or H$_2$C=C(CH$_3$)—CH$_2$—.

Good results can be achieved if the unsaturated silane compound comprises only one allyl group.

Especially preferred compounds are

H$_2$C=CH—CH$_2$Si(CH$_3$)$_3$ CAS: [762-72-1]
H$_2$C=CH—(CH$_2$)$_2$Si(CH$_3$)$_3$
H$_2$C=CH—(CH$_2$)$_3$Si(CH$_3$)$_3$
H$_2$C=CH—(CH$_2$)$_4$Si(CH$_3$)$_3$
H$_2$C=CH—(CH$_2$)$_8$Si(CH$_3$)$_3$
H$_2$C=CH—CH$_2$Si(i-C$_3$H$_7$)$_3$ CAS: [24400-84-8]
H$_2$C=CH—(CH$_2$)$_2$Si(i-C$_3$H$_7$)$_3$
H$_2$C=CH—(CH$_2$)$_3$Si(i-C$_3$H$_7$)$_3$
H$_2$C=CH—(CH$_2$)$_4$Si(i-C$_3$H$_7$)$_3$
H$_2$C=CH—(CH$_2$)$_8$Si(i-C$_3$H$_7$)$_3$
H$_2$C=CH—CH$_2$Si(CH$_3$)$_2$(t-C$_4$H$_9$)
H$_2$C=CH—(CH$_2$)$_2$Si(CH$_3$)$_2$(t-C$_4$H$_9$)
H$_2$C=CH—(CH$_2$)$_3$Si(CH$_3$)$_2$(t-C$_4$H$_9$)
H$_2$C=CH—(CH$_2$)$_4$Si(CH$_3$)$_2$(t-C$_4$H$_9$)
H$_2$C=CH—(CH$_2$)$_8$Si(CH$_3$)$_2$(t-C$_4$H$_9$)
H$_2$C=CH—CH$_2$Si(C$_2$H$_5$)$_3$
H$_2$C=CH—(CH$_2$)$_2$Si(C$_2$H$_5$)$_3$
H$_2$C=CH—(CH$_2$)$_3$Si(C$_2$H$_5$)$_3$
H$_2$C=CH—(CH$_2$)$_4$Si(C$_2$H$_5$)$_3$
H$_2$C=CH—(CH$_2$)$_8$Si(C$_2$H$_5$)$_3$
H$_2$C=CH—CH$_2$Si(CH$_3$)$_2$(n-C$_{18}$H$_{37}$)
H$_2$C=CH—(CH$_2$)$_2$Si(CH$_3$)$_2$(n-C$_{18}$H$_{37}$)
H$_2$C=CH—(CH$_2$)$_3$Si(CH$_3$)$_2$(n-C$_{18}$H$_{37}$)
H$_2$C=CH—(CH$_2$)$_4$Si(CH$_3$)$_2$(n-C$_{18}$H$_{37}$)
H$_2$C=CH—(CH$_2$)$_8$Si(CH$_3$)$_2$(n-C$_{18}$H$_{37}$)
H$_2$C=CH—CH$_2$Si(CH$_3$)$_2$(C$_6$H$_5$)
H$_2$C=CH—(CH$_2$)$_2$Si(CH$_3$)$_2$(C$_6$H$_5$)
H$_2$C=CH—(CH$_2$)$_3$Si(CH$_3$)$_2$(C$_6$H$_5$)
H$_2$C=CH—(CH$_2$)$_4$Si(CH$_3$)$_2$(C$_6$H$_5$)
H$_2$C=CH—(CH$_2$)$_8$Si(CH$_3$)$_2$(C$_6$H$_5$)
H$_2$C=CH—CH$_2$—O—Si(CH$_3$)$_3$
H$_2$C=CH—CH$_2$—O—Si(C$_2$H$_5$)$_3$
H$_2$C=CH—CH$_2$—O—Si(i-C$_3$H$_7$)$_3$

H$_2$C=CH—CH$_2$—O—Si(CH$_3$)$_2$(t-C$_4$H$_9$)
H$_2$C=CH—CH$_2$—O—Si(CH$_3$)$_2$(n-C$_{18}$H$_{37}$)
H$_2$C=CH—CH$_2$—O—Si(CH$_3$)$_2$(C$_6$H$_5$)
H$_2$C=CH—CH$_2$Si(CH$_3$)$_2$—O—Si(CH$_3$)$_3$
H$_2$C=CH—(CH$_2$)$_2$Si(CH$_3$)$_2$—O—Si(CH$_3$)$_3$
H$_2$C=CH—(CH$_2$)$_3$Si(CH$_3$)$_2$—O—Si(CH$_3$)$_3$
H$_2$C=CH—(CH$_2$)$_4$Si(CH$_3$)$_2$—O—Si(CH$_3$)$_3$
H$_2$C=CH—(CH$_2$)$_8$Si(CH$_3$)$_2$—O—Si(CH$_3$)$_3$
H$_2$C=CH—CH$_2$Si(CH$_3$)(—O—Si(CH$_3$)$_3$)$_2$
H$_2$C=CH—(CH$_2$)$_2$Si(CH$_3$)(—O—Si(CH$_3$)$_3$)$_2$
H$_2$C=CH—(CH$_2$)$_3$Si(CH$_3$)(—O—Si(CH$_3$)$_3$)$_2$
H$_2$C=CH—(CH$_2$)$_4$Si(CH$_3$)(—O—Si(CH$_3$)$_3$)$_2$
H$_2$C=CH—(CH$_2$)$_8$Si(CH$_3$)(—O—Si(CH$_3$)$_3$)$_2$
H$_2$C=CH—CH$_2$Si(—O—Si(CH$_3$)$_3$)$_3$
H$_2$C=CH—(CH$_2$)$_2$Si(—O—Si(CH$_3$)$_3$)$_3$
H$_2$C=CH—(CH$_2$)$_3$Si(—O—Si(CH$_3$)$_3$)$_3$
H$_2$C=CH—(CH$_2$)$_4$Si(—O—Si(CH$_3$)$_3$)$_3$
H$_2$C=CH—(CH$_2$)$_8$Si(—O—Si(CH$_3$)$_3$)$_3$
H$_2$C=CH—CH$_2$Si(OCH$_3$)$_3$
H$_2$C=CH—(CH$_2$)$_2$Si(OCH$_3$)$_3$
H$_2$C=CH—(CH$_2$)$_3$Si(OCH$_3$)$_3$
H$_2$C=CH—(CH$_2$)$_4$Si(OCH$_3$)$_3$
H$_2$C=CH—(CH$_2$)$_8$Si(OCH$_3$)$_3$
H$_2$C=CH—CH$_2$Si(OC$_2$H$_5$)$_3$
H$_2$C=CH—(CH$_2$)$_2$Si(OC$_2$H$_5$)$_3$
H$_2$C=CH—(CH$_2$)$_3$Si(OC$_2$H$_5$)$_3$
H$_2$C=CH—(CH$_2$)$_4$Si(OC$_2$H$_5$)$_3$
H$_2$C=CH—(CH$_2$)$_8$Si(OC$_2$H$_5$)$_3$
H$_2$C=CH—CH$_2$Si(C$_6$H$_5$)$_3$ CAS: [18752-21-1]
H$_2$C=CH—(CH$_2$)$_2$Si(C$_6$H$_5$)$_3$
H$_2$C=CH—(CH$_2$)$_3$Si(C$_6$H$_5$)$_3$
H$_2$C=CH—(CH$_2$)$_4$Si(C$_6$H$_5$)$_3$
H$_2$C=CH—(CH$_2$)$_8$Si(C$_6$H$_5$)$_3$
H$_2$C=C(CH$_3$)—CH$_2$Si(CH$_3$)$_3$ CAS: [18292-38-1]
(2-Cyclopentenyl)Si(CH$_3$)$_3$ CAS: [14579-08-9]
(Cyclopentadienyl)Si(CH$_3$)$_3$ CAS: [3559-74-8]
H$_2$C=CH—CH$_2$Si(p-C$_6$H$_4$OCH$_3$) CAS: [68469-60-3]
1-Allyl-,3,5,7,9,11,13,15-heptacyclopentyl-pentacyclo [9.5.1$^{3,9}$1$^{5,15}$.1$^{7,13}$]octasiloxan
1-Allyl-3,5,7,9,11,13,15-heptaisopropyl-pentacyclo [9.5.1$^{3,9}$1$^{5,15}$1$^{7,13}$]octasiloxan
H$_2$C=CH—CH$_2$Si(CH$_3$)$_2$H
H$_2$C=CH—(CH$_2$)$_2$Si(CH$_3$)$_2$H
H$_2$C=CH—(CH$_2$)$_3$Si(CH$_3$)$_2$H
H$_2$C=CH—(CH$_2$)$_4$Si(CH$_3$)$_2$H
H$_2$C=CH—(CH$_2$)$_8$Si(CH$_3$)$_2$H Without wishing to be bound to a particular mechanism, a possible explanation for the mechanism regarding the detectable reduction of hydrogen evolution by component (D) might be a slower hydrosilylation reaction caused by electronic and/or steric effects as compared to the Si—CH=CH$_2$-groups present in component (A). So the network of the impression material caused by reaction of component (A) with (B) catalyzed by component (C) forms first and residual Si—H-groups of component (B) are then removed by the somewhat slower hydrosilylation reaction of component (D).

This invention offers an efficient way to reduce hydrogen evolution especially during pouring gypsum models and improves the quality of gypsum models.

In two component VPS (vinyl polysiloxane) formulations the unsaturated silane compound can be used both in the base paste and in the catalyst paste which gives new degrees of freedom in the formulation of these materials.

The effectiveness of the unsaturated silane compound in reducing the amount of evolved hydrogen gas can be determined, in a practical sense as mentioned above, by inspection of a positive gypsum model formed from the impression. The positive model is substantially free of pits when the gypsum is poured into the impression preferably in less than about 2 hours, more preferably in less than about 30 minutes and most preferably in about 15 minutes after the start of extrusion of the impression material. Although the hardening or set time of the gypsum model material from the start of mixing with water will vary depending on the manufacturer and type of gypsum, the hardening time is generally about 30 minutes to one hour.

The invention provides therefore a low-cost material with regard to the state of the art suggesting to use—compared to nobel metal compounds—cheap organic compounds as hydrogen scavengers.

The terms "comprise" and "contain" within the meaning of the invention introduce a non exhaustive list of features. Likewise, the word "one" or "a" is to be understood in the sense of "at least one".

The term silicone as used herein, refers to a polymer having alternating silicon and oxygen atoms (i.e., a polysiloxane chemical structure) and having sufficient pendant functional groups to undergo a setting reaction in the presence of a crosslinker compound and a catalyst compound.

The term crosslinker as used herein, refers to polymers that react with the functional group or groups of the polymer chains simultaneously to lengthen them and connect them laterally, e.g., to form the crosslinked network characteristic of a silicone elastomer. In contrast to a thermoplastic polymer (i.e., a polymer that softens and flows upon heating) a crosslinked polymer, after crosslinking, is incapable characteristically of further flow.

The term hydrosilylation means the addition of an organosilicon hydride compound to a compound containing an aliphatic multiple bond (e.g., an olefinic or acetylenic unsaturation), preferably a vinyl group, —CH=CH$_2$ or allyl group.

The addition-curable compounds (A) of the invention generally are synthetic polymeric silicone materials that possess an extraordinarily wide range of physical properties. They can be low- or high-viscosity liquids, solid resins, or vulcanizable gums. They display an unusual combination of organic and inorganic chemical properties that are due to their unique molecular structure of alternating silicon and oxygen atoms.

Suitable silicone polymers are well-known in the art and are described, for example, in "Silicones," Kirk-Othmer Encyclopedia of Chemical Technology, 3rd Ed., 20, 922-962 (1982).

The preparation of these molecules is generally known to the skilled person. The preparation of corresponding molecules can be achieved, e.g., according to standard procedures which are portrayed in W. Noll, "Chemie und Technologie der Silikone", Verlag Chemie Weinheim 2. edition 1964, pages 162-206 or J. Burghardt, Chemie und Technologie der Polysiloxane in "Silikone, Chemie und Technologie", Vulkan Verlag, Essen, 1989, pages 23-37.

The typical polymeric silicone material is a siloxane polymer depicted in the formula below:

(II)

in which the radicals R in formula (II) independently from each other represent a non-substituted or substituted monovalent hydrocarbon group with 1 to 6 C atoms, which is preferably free from aliphatic multiple bonds and n is generally in the range of 5 to 2500, preferably in the range of 10 to 1600.

Generally, the radicals R in formula (II) can represent any non-substituted or substituted monovalent hydrocarbon group with 1 to 6 C atoms. Corresponding non-substituted or substituted monovalent hydrocarbon group with 1 to 6 C atoms can be linear or, if the number of Carbon atoms exceeds 2, branched or cyclic. Generally, the radicals R can be equipped with all types of substituents that do not interfere with at least one of the remaining consituents of the composition and do not interfere with the curing reaction. The term "interfere" as used in the context of the present text relates to any influence of such a substituent on at least one of the remaining consituents of the composition or the curing reaction, or both, which is detrimental to the properties of the hardened product. The term "detrimental" as used in the context of the present text relates to a change of properties of the precursors or the cured product that affect the usefulness of the precursors or the cured product related to the intended use of the precursors or the cured product in a negative manner.

The addition-curable compound mentioned above can be used alone or as mixture of different addition-curable compounds, preferably as mixture of polydimethylsiloxane compounds having different viscosities.

The preferred amount of the addition-curable compound varies depending upon the desired physical properties of the silicone composition (such as the desired uncured viscosity, cured hardness, etc.). In part due to the wide range of acceptable molecular weights for the polymer component and the many types of adjuvants which may be added to the polymer, this amount can vary widely.

Based on the total weight of the composition, the presently preferred amount of organopolysiloxane compound is between about 5% and about 99%, or between about 10% and about 90%, or between about 20% and about 80% by weight.

The molecular weight ($M_w$) of component (A) before curing can be in the range of about 600 to about 200000 g/mol, or in the range of about 1000 to about 1000000 g/mol.

The molecular weight ($M_w$) can be determined with GPC. Appropriate methods are know by the expert. In addition the determination of the molecular weight is possible using nuclear magnetic resonance spectroscopy (end-group determination).

The viscosity of the addition-curable compound according to component (A) can be in the range of about 5 to about 200000 mPas, or in the range of about 10 to about 165000 mPas, or in the range of about 200 to about 10000 mPas, measured according to DIN 53018-1.

A preferred method of measurement, however, is performed with Haake Rotovisco RV20 (spindle MV, measuring cup NV). The viscosity is measured at 23° C. After activation and rectification of the system, spindle MV is installed. Following, the material to be measured is filled into the measuring cup NV. Without undue delay, the spindle is lowered into the measuring cup NV. The spindle should be covered by a layer of max. 1 mm. The material to be measured is tempered for 20 min at 23° C. The measurement is started and the viscosity values (mPas) are recorded starting 20 s after the start of measurement. It has to be taken care of that at no time the measuring cup NV itself may rotate or move at all. A value for the viscosity is obtained in mPas. The above mentioned method of measurement corresponds to DIN 53018-1.

The crosslinker (B) contains at least two silicon-hydrogen linkages and can be a polymeric compound or a compound that is not polymeric. These compounds are well known in the art and are disclosed, for example in U.S. Pat. No. 3,159,662, U.S. Pat. No. 3,220,972 and U.S. Pat. No. 3,410,886.

Some classes of crosslinker having at least two silicon-bonded hydrogen atoms which can be used in the invention are (a) organohydrosilanes having the empirical formula, $(H)_a(R^3)_b(Si)_c$ wherein each $R^3$ can be the same or different and represents an organic group, preferably selected from monovalent hydrocarbyl groups, monovalent alkoxy hydrocarbyl groups and halogenated monovalent hydrocarbyl groups; c represents an integer having a value at least 1, a represents an integer having a value at least 2, and the sum of a and b equals the sum of 2 and two times c, (b) organohydrocyclopolysiloxanes having the empirical formula, $(H)_d(R^3)_e(SiO)_f$ wherein $R^3$ is as defined above, f represents an integer having a value from 3 to 18, d represents an integer having a value at least 2 and preferably less than or equal to f, and the sum of d and e equals two times f, and (c) organohydropolysiloxane polymers or copolymers having the empirical formula $(H)_g(R^3)_h(Si)_jO_{(j-1)}$ wherein $R^3$ is as defined above, j represents an integer having a value from 2 to 10.000, g represents an integer having a value at least 2 and less than or equal to j, and the sum of g and h equals the sum of 2 and two times j.

Among, the groups represented by $R^3$ include, for example, straight-chain and branched alkyl groups having 1 to 18 carbon atoms, e.g., methyl, ethyl, propyl, 1 butyl, hexyl, dodecyl, octy], and octadecyl, cycloalkyl groups having 5 to 8 ring carbon atoms, e.g., cyclohexyl and cyclooctyl, aryl, aralkyl, and alkaryl groups having 6 to 18 carbon atoms, e.g., phenyl, naphthyl, tolyl, xylyl, benzyl and phenylethyl, and halo-substituted groups thereof, e.g., chloromethyl, chlorophenyl, and dibromophenyl. Preferably, the $R^3$ group includes methyl and phenyl. More preferably, the $R^3$ group is methyl. The $R^3$ group can also be an unsaturated aliphatic group having 2 to 20 carbon atoms, such as alkeny) or cycloalkenyl, e.g., vinyl, allyl and cyclohexenyl. When the $R^3$ group is a group with allphatic unsaturation, the silicon compound containing silicon-hydrogen linkages can be reacted with itself to form a crosslinked structure or network.

The amount of the crosslinker should be sufficient to provide the desired degree of crosslinking of the silicone composition. In part due to the wide range of acceptable molecular weights for the adition-curable compound and/or the crosslinker, it is presently believed that this amount is best described in terms of the ratio of SiH groups to functional (e.g., vinyl) groups in the composition.

The presently preferred ratio of SiH groups to functional groups is between about 1:about 1 and about 20:about 1, or between about 1:about 1 and about 10: about 1 and or between about 1.3:about 1 and about 4:about 1.

A preferred amount of crosslinker component in the total composition is between about 0.2% and about 90% by weight, more preferably between about 0.2% and about 20% by weight and most preferably between about 0.2% and about 10% by weight.

Suitable hydrosilation catalysts (C) for use in the invention include those compounds which promote or facilitate the addition reaction between the ethylenically unsaturated groups and the silicon-bonded hydrogen groups.

The catalyst preferably contains Pt and is a Karsted catalyst. The catalyst can be prepared from hexachloroplatinum acid by reduction with tetramethyldivinyl-disiloxane. Such compounds are known to the skilled person. Any other platinum compounds which catalyze or accelerate addition crosslinking of silanes with ethylenically unsaturated double bonds are also suitable. Platinum-siloxane complexes as described, e.g. in U.S. Pat. No. 3,715,334, U.S. Pat. No. 3,775,352 and U.S. Pat. No. 3,814,730 are suitable, for example. The disclosure of these patents with regard to platinum complexes and their preparation is explicitly mentioned and expressly regarded as part of the disclosure of the present text.

The amount of the platinum complex catalyst should be sufficient to provide the desired degree of crosslinking of the organopolysiloxane compound within a reasonable time. In part due to the wide range of acceptable molecular weights for the addition-curable compound, it is presently believed that this amount is best described in terms of the ratio of Pt atoms to functional groups in the composition.

The platinum catalyst is preferably used in quantities of about 0.00005 to about 0.05% by weight, or about 0.0002 to about 0.04% by weight, each calculated as elemental platinum and related to the overall weight of the composition.

Examples of suitable catalysts include platinum or platinum compound catalysts exemplified by chloroplatinic acid, a complex of chloroplatinic acid and an alcohol, a complex of platinum and an olefin, a complex of platinum and a ketone, a complex of platinum and a vinylsiloxane, colloidal platinum, a complex of colloidal platinum and a vinylsiloxane etc., palladium, a mixture of palladium black and triphenylphosphine, etc., or rhodium or rhodium compound catalysts.

Especially preferred is a complex of Pt with 1,1,3,3-tetramethyl divinyldisiloxane.

To control the reactivity of the addition reaction and to prevent premature curing, it may be advantageous to add an inhibitor (E) which prevents the addition reaction for a specific period of time or slows the addition reaction down. Such inhibitors are known and described, e.g. in U.S. Pat No. 3,933,880, the disclosure of which regarding such inhibitors and their preparation is expressly regarded as being part of the disclosure of the present invention.

Examples of such inhibitors are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on an vinyl siloxane are 1,1,3,3-tetramethyl-1,3-divinyl siloxane and poly-, oligo- and disiloxanes containing vinyl groups.

The inhibitor can be present in an amount of up to about 0.3% by weight based on the composition, or in an amount of up to about 0.12% by weight.

The compositions of the invention also include a filler (F), preferably a mixture of hydrophobic fillers. A wide variety of inorganic, hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4 to 6 µm); amorphous silicone dioxides, such as a diatomaceous earth (4 to 7 µm); and silanated fumed silica, such as Cab-o-Sil TS-530 (160-240 m²/g), manufactured by Cabot Corporation.

The sizes and surface areas of the foregoing materials are controlled to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or silazides.

Such fillers can be present in amounts of from about 10 to about 90% by weight, or about 20 to about 80 or about 30 to about 75% by weight of the composition.

Among the fillers which can be used are non-reinforcing fillers such as quartz, cristobalite, calcium silicate, diatomaceous earth, zirconium silicate, montmorillonite such as bentonite, zeolite, including moleculer sieves such as sodium aluminium silicate, metal oxide powder such as aluminium or zinc oxide or their mixed oxides, barium sulphate, calcium carbonate, plaster, glass and plastic powder.

Suitable fillers are also reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than 50 µm.

A combination of reinforcing and non-reinforcing fillers is particularly preferred. In this respect, the quantity of reinforcing fillers ranges from about 1 to about 10% by weight or from about 2 to about 5% by weight.

The difference in the named overall ranges, i.e. about 9 to about 80% by weight is accounted for by non-reinforcing fillers.

Pyrogenically-prepared highly-disperse silicic acids which have preferably been hydrophobized by surface treatment are preferred as reinforcing fillers. The surface treatment can be carried out, for example with dimethyldichlorosilane, hexamethyidisilazane, tetramethylcyclotetrasiloxane or polymethylsiloxane.

Particularly preferred non-reinforcing fillers are quartzes, cristobalites, calcium carbonate and sodium aluminium silicates which can be surface-treated. The surface treatment can generally be carried out with the same methods as described in the case of the strengthening fillers.

Optionally additives (G) like modifiers, dyes, pigments, thixotropic agents, flow improvers, polymeric thickeners, surfactants, odorous substances, diluting agent(s) and flavourings can be added alone or in admixture, to adjust especially the Theological characteristics.

The additive(s) can be present in an amount in the range of about 0.05 to about 90% by weight, or in the range of about 0.1 to about 40% by weight with respect to the cured composition.

The shore hardness A of the cured composition of the invention measured according to DIN 53505 60 min after mixing the components can be in the range of about 30 to about 95, or in the range of about 35 to about 90 more or in the range of about 40 to about 80 (specimen: disc with a diameter of 38 mm and a height of 6 mm; measurement taken 24 h after mixing the components).

Figure 1:
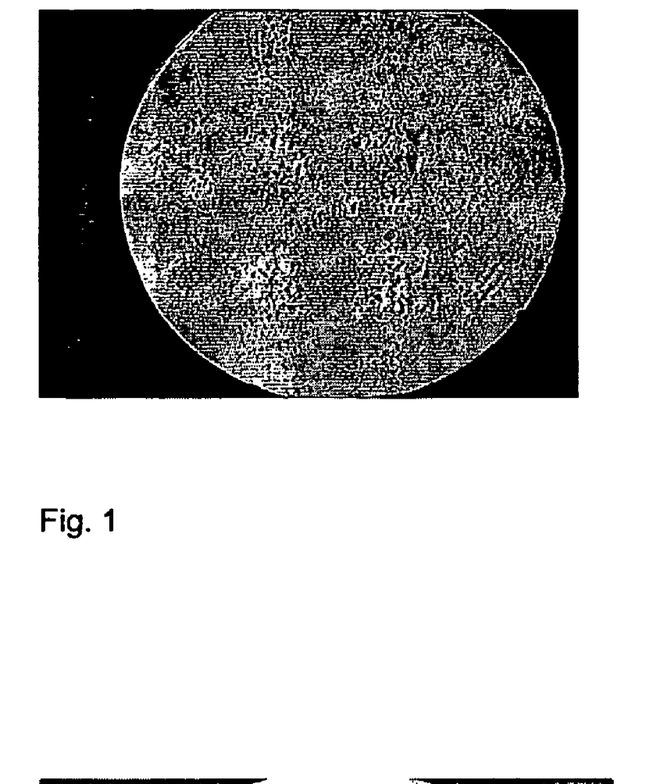
FIG. 1 is a picture of a gypsum model not containing component (D).
Figure 2:
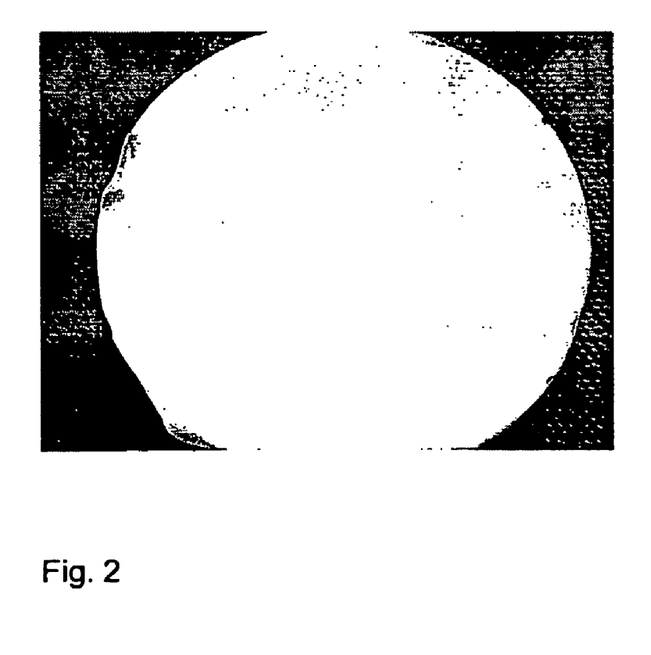
FIG. 2 is a picture of a gypsum model obtained from an impression comprising component (D).
Figure 3:
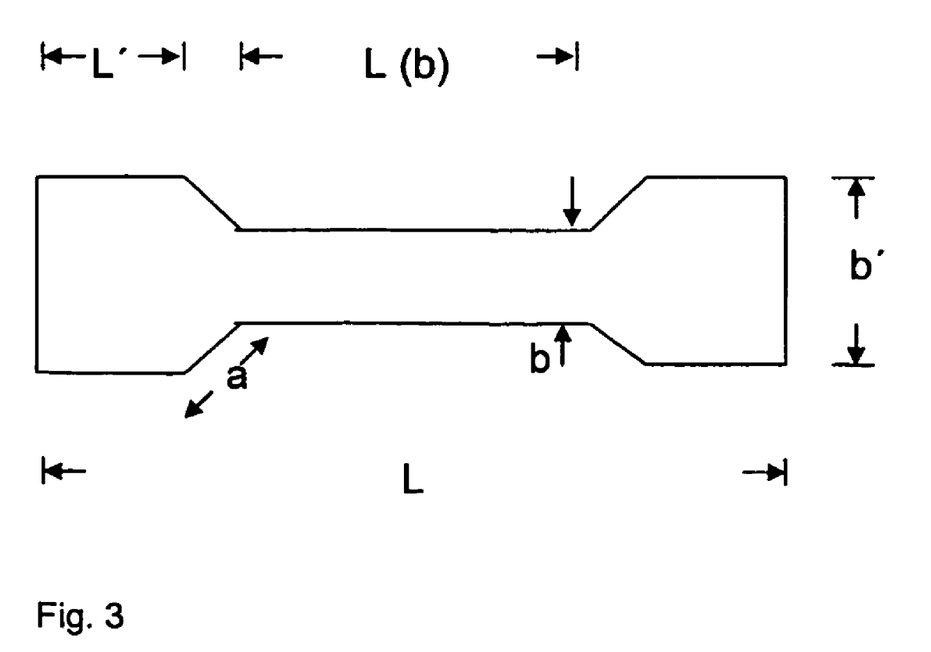
FIG. 3 is a picture of a specimen used in the measurement of elongation at break and tensile strength

The elongation at break of the cured composition of the invention measured according to DIN 50125 120 min after mixing the components can be in the range of about 50 to about 300, or in the range of about 60 to about 250 or in the range of about 80 to about 200% (specimen as described in FIG. 3 with L=75 mm, L'=17 mm, b=4 mm, b'=12 mm, L(b)=30 mm, a=6 mm, thickness: 2 mm; measurement taken 24 h after mixing the components).

The tensile strength of the cured composition of the invention measured according to DIN 50125 120 min after mixing the components can be in the range of about 0.5 to about 5, or in the range of about 0.7 to about 5 or in the range of about 1 to about 4.5 MPa (specimen as described in FIG. 3).

Preferably, the inventive composition is able to set at ambient conditions, more preferably at a temperature within the range of about 15 to 45° C. or at a temperature existing in a patient's mouth, that is at body temperature which can be within a range of about 30 to about 40° C.

Preferably, setting of the composition can be accomplished within 1 to 10 minutes or within 2 to 5 minutes.

If used as dental impression material, the composition of the invention is generally pre-mixed into preferably two parts prior to use. For example, one part may contain the vinyl-containing organopolysiloxane, the platinum catalyst and the allyl compound, while the other part may contain the organohydrogenpolysiloxane crosslinker and optionally vinyl-containing organopolysiloxane.

Therefore, the invention also relates to a kit of parts, comprising a base part (I) and a catalyst part (II), wherein the base part (I) comprises components (A) and (B), and the catalyst part (II) comprises component (C), and wherein component (D) is present either in the base part or the catalyst part or in the base part and the catalyst part. The other optional components (E), (F), (G) can be present in the base part or the catalyst part or in the base part and the catalyst part.

The invention also relates to a method of producing a curable composition comprising the steps i) providing components a), b), c) and d), ii) mixing the components.

The dosing of the components can be carried out by sight (strand-length comparison), by weight, via pre-dosed pack units and subsequent manual mixing, from double-chambered cartridges with static mixing tubes or by means of volume dosing systems with downstream static or dynamic mixers. A suitable dynamic mixing device is described in EP 0 492 413 B1 and available on the market as Pentamix™ or Pentamix™ 2.

In practice, the impression material can be syringed through a static or mechanical mixing device into an impression tray or onto patients teeth or tissue and placed in the patients mouth. After the impression material is set, the tray is removed from the patient's mouth and, in instances where the dental practitioner prepares the positive model, it may be preferable to pour the positive model material immediately after removal of the impression from the patient's mouth. However, it is also possible to disinfect the impression prior to pouring the model material. Although it is generally referred to as "Immediate pour," in a practical sense, this means that the positive model material is poured into the impression in about 15 minutes. More frequently, the positive model material is poured into the impression in about 30 minutes to 2 hours after making the impression. Sometimes it last up to 12 h until the impression is poured.

The invention therefore also relates to a method of making a positive model, especially a dental model comprising the steps of
 a) providing a composition containing an addition-curable compound (A), a crosslinker (B), a catalyst (C) and an unsaturated silane compound (D) with at least one methylene group directly attached to the unsaturation in an amount effective to reduce the amount of hydrogen gas evolved in the reaction of compounds mentioned,
 b) contacting the composition with a surface to obtain a negative model,
 c) curing the composition,
 d) pouring the negative model after removal of the cured composition from the surface with a pouring composition such as gypsum to obtain a positive model.

Thus, the invention provides compositions (e.g., silicone compositions) which are useful for preparing sealants, caulks, adhesives, coatings, impression materials, molding materials, lithographic plates, release liners, potting materials and reflective sheets. Preferred applications of this invention include areas in which non-stick or low-energy properties of a surface are required such as impression materials, modeling materials or in release coatings for use with pressure-sensitive adhesives.

The composition of the invention does not necessarily comprise palladium hydrogen scavengers. There is also no absolute need for Pt black. Due to the reduction of hydrogen evolution the composition has an improved tear strength. Therefore, there is no absolute need to add a considerable amount of VQM based compounds for improving the tear strength.

There is also no absolute need to add epoxy containing compounds.

The invention is hereinafter described by examples.

Measurements

The effectiveness of reducing the evolution of hydrogen gas was determined by counting the bubbles on a gypsum model caused by hydrogen evolution from the negative mold as described below.

Automixable VPS Impression Materials

In a conventional mixing unit (Speedmixer DAC 150 FVZ) several base and catalyst pastes were manufactured by mixing the following raw materials resulting in a homogenous paste.

EXAMPLE A

| Base paste | |
|---|---|
| Raw Material | % (weight) |
| Vinylterminated polydimethylsiloxane (1000 cSt) | 15.1 |
| Vinylterminated polydimethylsiloxane (200 cSt) | 12.0 |
| Poly(methyl)(hydrogen)siloxane (200 cSt; 0.20% $H_2$) | 7.5 |
| Polyethersiloxane-Surfactant Silwet L77 | 0.4 |
| Pigment Dispersion | 1.0 |
| Pyrogenic Silica (hydrophobized, 100 $m^2/g$) | 6.4 |
| Quartz (hydrophobized, <11 μm) | 56.1 |
| Allyltrimethylsilane | 1.5 |

| Catalyst paste | |
|---|---|
| Raw Material | % (weight) |
| Vinylterminated polydimethylsiloxane (200 cSt) | 30.0 |
| Platin-Tetramethyldivinyldisiloxane-komplex (1.3 weight-% Pt) in silicone oil | 4.0 |
| Pigment Dispersion | 1.5 |
| Pyrogenic Silica (hydrophobized, 100 $m^2/g$) | 5.0 |
| Natrium-Aluminium-Silicate filler (1.7 $m^2/g$) | 59.5 |

EXAMPLE B

Comparative Example

| Base paste | |
|---|---|
| Raw Material | % (weight) |
| Vinylterminated polydimethylsiloxane (1000 cSt) | 16.2 |
| Vinylterminated polydimethylsiloxane (200 cSt) | 12.4 |
| Poly(methyl)(hydrogen)siloxane (200 cSt; 0.20% $H_2$) | 7.5 |

-continued

Base paste

| Raw Material | % (weight) |
|---|---|
| Polyethersiloxane-Surfactant Silwet L77 | 0.4 |
| Pigment Dispersion | 1.1 |
| Pyrogenic Silica (hydrophobized, 100 m$^2$/g) | 6.4 |
| Quartz (hydrophobized, <11 μm) | 56.0 |

Catalyst Paste

Identical to Example A

EXAMPLE C

Comparative Example

Base Paste

Identical to Example B

Catalyst paste

| Raw Material | % (weight) |
|---|---|
| Vinylterminated polydimethylsiloxane (200 cSt) | 29.4 |
| Platin-Tetramethyldivinyldisiloxane-komplex (1,3 weight-% Pt) in silicone oil | 4.0 |
| Pigment Dispersion | 1.5 |
| Pyrogenic Silica (hydrophobized, 100 m$^2$/g) | 5.0 |
| Natrium-Aluminium-Silicate filler (1.7 m$^2$/g) | 59.4 |
| Pd-Dispersion | 0.2 |

(1% Pd (submicron powder, 99.9+%) and 10% pyrogenic silica (100 m$^2$/g) in silicone oil (200 cSt))

Base and catalyst pastes were mixed to homogeneity in a volume ratio of 5:1 (v/v base:catalyst) and filled into a mold with a diameter of 3.8 cm and a height of 6 mm. After setting of the material the mold was filled with gypsum suspension. After the gypsum had set, it was removed from the mold and the bubbles caused by the evolution of hydrogen on the surface were counted. The results are summarized in the following table:

TABLE 1

| | Example A (with component (D)) | Example B (without component (D)) | Example C (with Pd metal) |
|---|---|---|---|
| Poured 15 minutes after mixing | about <10 bubbles/cm$^2$ | about >100 bubbles/cm$^2$ | about <100 bubbles/cm$^2$ |
| Poured 120 minutes after mixing | about <10 bubbles/cm$^2$ | about >100 bubbles/cm$^2$ | about >20 bubbles/cm$^2$ |

These results show the effectiveness of the addition of component (D) in comparison to the hydrogen absorption achieved by Pd metal.

VPS Impression Materials for Cartridge Application

EXAMPLE D

Base paste

| Raw Material | % (weight) |
|---|---|
| Vinylterminated polydimethylsiloxane (7000 cSt) | 24.75 |
| Vinylterminated polydimethylsiloxane (200 cSt) | 19.0 |
| Poly(methyl)(hydrogen)siloxane (1.78 mmol/g Si—H; 50 cSt) | 6.0 |
| Poly(methyl)(hydrogen)siloxane (4.0 mmol/g Si—H; 100 cSt) | 7.0 |
| Polydimethylsiloxane (10 cSt) | 7.75 |
| Polyether Surfactant | 1.5 |
| Pigment | 0.5 |
| Pyrogenic Silica (hydrophobized, 100 m$^2$/g) | 4.0 |
| Hydrophobized cristoballit filler (Average particle size: 3 μm) | 29.5 |

Catalyst paste

| Raw Material | % (weight) |
|---|---|
| Vinylterminated polydimethylsiloxane (7000 cSt) | 27.5 |
| Vinylterminated polydimethylsiloxane (200 cSt) | 13.2 |
| Polydimethylsiloxane (10 cSt) | 3.8 |
| Platin-Tetramethyldivinyldisiloxane-komplex (1.3 weight-% Pt) in silicone oil | 1.6 |
| Pigment | 0.1 |
| Pyrogenic Silica (hydrophobized, 100 m$^2$/g) | 2.6 |
| Cristoballit filler (Average particle size: 3 μm) | 49.9 |
| Tetraallylsilane | 0.5 |
| Allyltrimethylsilane | 0.8 |

EXAMPLE E

Comparative Example

Base Paste

Identical to Example D

Catalyst paste

| Raw Material | % (weight) |
|---|---|
| Vinylterminated polydimethylsiloxane (7000 cSt) | 27.5 |
| Vinylterminated polydimethylsiloxane (200 cSt) | 13.8 |
| Polydimethylsiloxane (10 cSt) | 4.0 |
| Platin-Tetramethyldivinyldisiloxane-komplex (1.3 weight-% Pt) in silicone oil | 1.6 |
| Pigment | 0.1 |
| Pyrogenic Silica (hydrophobized, 100 m$^2$/g) | 2.6 |
| Cristoballit filler (Average particle size: 3 μm) | 49.9 |
| Tetraallylsilane | 0.5 |

Base and catalyst pastes were mixed to homogeneity in a volume ratio of 1:1 (v/v base:catalyst) and filled into a mold with a diameter of 3.8 cm and a height of 6 mm. After setting of the material the mold was filled with gypsum suspension. After the gypsum had set, bubbles caused by the evolution of hydrogen were counted. The results are summarized in the following table:

TABLE 2

|  | Example D (with component (D)) | Example E (without component (D)) |
|---|---|---|
| Poured 15 minutes after mixing | about <10 bubbles/cm² | about >100 bubbles/cm² |
| Poured 120 minutes after mixing | about <10 bubbles/cm² | about >100 bubbles/cm² |

The figures visualize the advantageous effect of the present invention.

The invention claimed is:

1. A composition comprising:
   a) an addition-curable siloxane compound (A),
   b) a siloxane crosslinker (B),
   c) a catalyst (C), and
   d) an unsaturated silane compound (D) with at least one methylene group directly attached to the unsaturation;
   wherein the composition does not contain an acetylenic alcohol containing at least 6 carbon atoms;
   wherein the composition sets at a temperature within the range of about 15 to 45° C.; and
   wherein the unsaturated silane compound (D) has the following structure:

$R^2R^3C\!=\!CR^1\text{-}A\text{-}SiR_3$ wherein
   R can be different or equal and is H, a monovalent alkyl ($C_1$-$C_{22}$), aryl ($C_6$-$C_{12}$), or O—$SiR^4_3$ group, optionally comprising heteroatoms, with the proviso that R is not an alkoxy group or an aryloxy group,
   $R^1$, $R^2$, $R^3$ can be different or equal and is H, a monovalent alkyl ($C_1$-$C_{22}$), or aryl ($C_6$-$C_{12}$) group, optionally comprising heteroatoms,
   $R^4$ is a monovalent alkyl ($C_1$-$C_{22}$) or aryl ($C_6$-$C_{12}$) group, wherein two or three of the residues $R^4$ in O—$SiR^4_3$ can combine to a cyclic or polycyclic structure,
   A is a divalent linear, branched or cyclic hydrocarbon group ($C_1$-$C_{12}$), optionally comprising an aromatic moiety, with at least one methylene group directly attached to the unsaturation, optionally comprising O-Atoms.

2. The composition of claim 1, further comprising an inhibitor (E).

3. The composition of claim 1, further comprising a filler (F).

4. The composition of claim 1, further comprising an additive (G) selected from modifiers, dyes, pigments, thixotropic agents, flow improvers, polymeric thickeners, surfactants, odorous substances, diluting agent(s) and/or flavorings.

5. The composition according to claim 1, wherein the unsaturated silane compound (D) is present in an amount such that the hydrogen gas evolution value of said composition in 2 hours per 10.0 g of the composition is less than about 0.6 ml.

6. The composition according to claim 1, wherein the unsaturated silane compound (D) is monofunctional.

7. The composition according to claim 1, wherein the unsaturated silane compound (D) comprises the structural element C=CH—$CH_2$ or C=C($CH_3$)—$CH_2$.

8. The composition according to claim 1, wherein the molecular weight of unsaturated silane compound (D) is below or up to about 1000 gmol$^{-1}$.

9. The composition according to claim 1, wherein the unsaturated silane compound (D) has a viscosity below or up to about 200 mPas, at 23° C.

10. The composition according to claim 1, wherein the unsaturated silane compound (D) is selected from:

$H_2C\!=\!CH\!-\!CH_2Si(CH_3)_3$,
$H_2C\!=\!CH\!-\!(CH_2)_2Si(CH_3)_3$,
$H_2C\!=\!CH\!-\!(CH_2)_3Si(CH_3)_3$,
$H_2C\!=\!CH\!-\!(CH_2)_4Si(CH_3)_3$,
$H_2C\!=\!CH\!-\!(CH_2)_8Si(CH_3)_3$,
$H_2C\!=\!CH\!-\!CH_2Si(i\text{-}C_3H_7)_3$,
$H_2C\!=\!CH\!-\!(CH_2)_2Si(i\text{-}C_3H_7)_3$,
$H_2C\!=\!CH\!-\!(CH_2)_3Si(i\text{-}C_3H_7)_3$,
$H_2C\!=\!CH\!-\!(CH_{24}Si(i\text{-}C_3H_7)_3$,
$H_2C\!=\!CH\!-\!(CH_2)_8Si(i\text{-}C_3H_7)_3$,
$H_2C\!=\!CH\!-\!CH_2Si(CH_3)_2(t\text{-}C_4H_9)$,
$H_2C\!=\!CH\!-\!(CH_2)_2Si(CH_3)_2(t\text{-}C_4H_9)$,
$H_2C\!=\!CH\!-\!(CH_2)_3Si(CH_3)_2(t\text{-}C_4H_9)$,
$H_2C\!=\!CH\!-\!(CH_2)_4Si(CH_3)_2(t\text{-}C_4H_9)$,
$H_2C\!=\!CH\!-\!(CH_2)_8Si(CH_3)_2(t\text{-}C_4H_9)$,
$H_2C\!=\!CH\!-\!CH_2Si(C_2H_5)_3$,
$H_2C\!=\!CH\!-\!(CH_2)_2Si(C_2H_5)_3$,
$H_2C\!=\!CH\!-\!(CH_2)_3Si(C_2H_5)_3$,
$H_2C\!=\!CH\!-\!(CH_2)_4Si(C_2H_5)_3$,
$H_2C\!=\!CH\!-\!(CH_2)_8Si(C_2H_5)_3$,
$H_2C\!=\!CH\!-\!CH_2Si(CH_3)_2(n\text{-}C_{18}H_{37})$,
$H_2C\!=\!CH\!-\!(CH_2)_2Si(CH_3)_2(n\text{-}C_{18}H_{37})$,
$H_2C\!=\!CH\!-\!(CH_2)_3Si(CH_3)_2(n\text{-}C_{18}H_{37})$,
$H_2C\!=\!CH\!-\!(CH_2)_4Si(CH_3)_2(n\text{-}C_{18}H_{37})$,
$H_2C\!=\!CH\!-\!(CH_2)_8Si(CH_3)_2(n\text{-}C_{18}H_{37})$,
$H_2C\!=\!CH\!-\!CH_2Si(CH_3)_2(C_6H_5)$,
$H_2C\!=\!CH\!-\!(CH_2)_2Si(CH_3)_2(C_6H_5)$,
$H_2C\!=\!CH\!-\!(CH_2)_3Si(CH_3)_2(C_6H_5)$,
$H_2C\!=\!CH\!-\!(CH_2)_4Si(CH_3)_2(C_6H_5)$,
$H_2C\!=\!CH\!-\!(CH_2)_8Si(CH_3)_2(C_6H_5)$,
$H_2C\!=\!CH\!-\!CH_2\!-\!O\!-\!Si(CH_3)_3$,
$H_2C\!=\!CH\!-\!CH_2\!-\!O\!-\!Si(C_2H_5)_3$,
$H_2C\!=\!CH\!-\!CH_2\!-\!O\!-\!Si(i\text{-}C_3H_7)_3$,
$H_2C\!=\!CH\!-\!CH_2\!-\!O\!-\!Si(CH_3)_2(t\text{-}C_4H_9)$,
$H_2C\!=\!CH\!-\!CH_2\!-\!O\!-\!Si(CH_3)_2(n\text{-}C_{18}H_{37})$,
$H_2C\!=\!CH\!-\!CH_2\!-\!O\!-\!Si(CH_3)_2(C_6H_5)$,
$H_2C\!=\!CH\!-\!CH_2Si(CH_3)_2\!-\!O\!-\!Si(CH_3)_3$,
$H_2C\!=\!CH\!-\!(CH_2)_2Si(CH_3)_2\!-\!O\!-\!Si(CH_3)_3$,
$H_2C\!=\!CH\!-\!(CH_2)_3Si(CH_3)_2\!-\!O\!-\!Si(CH_3)_3$,
$H_2C\!=\!CH\!-\!(CH_2)_4Si(CH_3)_2\!-\!O\!-\!Si(CH_3)_3$,
$H_2C\!=\!CH\!-\!(CH_2)_8Si(CH_3)_2\!-\!O\!-\!Si(CH_3)_3$,
$H_2C\!=\!CH\!-\!CH_2Si(CH_3)(\!-\!O\!-\!Si(CH_3)_3)_2$,
$H_2C\!=\!CH\!-\!(CH_2)_2Si(CH_3)(\!-\!O\!-\!Si(CH_3)_3)_2$,
$H_2C\!=\!CH\!-\!(CH_2)_3Si(CH_3)(\!-\!O\!-\!Si(CH_3)_3)_2$,
$H_2C\!=\!CH\!-\!(CH_2)_4Si(CH_3)(\!-\!O\!-\!Si(CH_3)_3)_2$,
$H_2C\!=\!CH\!-\!(CH_2)_8Si(CH_3)(\!-\!O\!-\!Si(CH_3)_3)_2$,
$H_2C\!=\!CH\!-\!CH_2Si(\!-\!O\!-\!Si(CH_3)_3)_3$,
$H_2C\!=\!CH\!-\!(CH_2)_2Si(\!-\!O\!-\!Si(CH_3)_3)_3$,
$H_2C\!=\!CH\!-\!(CH_2)_3Si(\!-\!O\!-\!Si(CH_3)_3)_3$,
$H_2C\!=\!CH\!-\!(CH_2)_4Si(\!-\!O\!-\!Si(CH_3)_3)_3$,
$H_2C\!=\!CH\!-\!(CH_2)_8Si(\!-\!O\!-\!Si(CH_3)_3)_3$,
$H_2C\!=\!CH\!-\!CH_2Si(C_6H_5)_3$,
$H_2C\!=\!CH\!-\!(CH_2)_2Si(C_6H_5)_3$,
$H_2C\!=\!CH\!-\!(CH_2)_3Si(C_6H_5)_3$,
$H_2C\!=\!CH\!-\!(CH_2)_4Si(C_6H_5)_3$,
$H_2C\!=\!CH\!-\!(CH_2)_8Si(C_6H_5)_3$,
$H_2C\!=\!C(CH_3)\!-\!CH_2Si(CH_3)_3$,
(2-Cyclopentenyl)$Si(CH_3)_3$,
(Cyclopentadienyl)$Si(CH_3)_3$, H$_2$C=CH—CH$_2$Si(p-C$_6$H$_4$OCH$_3$),
1-Allyl-,3,5,7,9,11,13,15-heptacyclopentyl-pentacyclo [9.5.1$^{3,9}$1$^{5,15}$.1$^{7,13}$]octasiloxan,
1-Allyl-3,5,7,9,11,13,15-heptaisopropyl-pentacyclo [9.5.1$^{3,9}$1$^{5,15}$.1$^{7,13}$]octasiloxan,
H$_2$C=CH—CH$_2$Si(CH$_3$)$_2$H,
H$_2$C=CH—(CH$_2$)$_2$Si(CH$_3$)$_2$H,
H$_2$C=CH—(CH$_2$)$_3$Si(CH$_3$)$_2$H,
H$_2$C=CH—(CH$_2$)$_4$Si(CH$_3$)$_2$H, and
H$_2$C=CH—(CH$_2$)$_8$Si(CH$_3$)$_2$H.

11. The composition according to claim 1, wherein the molecular weight of component (A) before curing is in the range of about 600 to about 200000 g/mol.

12. The composition according to claim 1 having a shore hardness A of the cured composition measured according to DIN 53505 60 min after mixing the components in the range of about 30 to about 95.

13. The composition according to claim 1 having a tensile strength of the cured composition measured according to DIN 50125 120 min after mixing the components in the range of about 0.5 to about 5 MPa.

14. The composition according to claim 1, wherein said composition is selected from the group consisting of impression materials and molding materials.

15. The composition of claim 1, wherein composition comprises an amount of the unsaturated silane compound (D) from 0.001% to 10% by weight with respect to the cured composition.

16. A kit of parts, comprising a base part (I) and a catalyst part (II), wherein the base part (I) comprises an addition-curable siloxane compound and a siloxane crosslinker, and the catalyst part (II) comprises a catalyst, wherein the kit further comprises an unsaturated silane compound with at least one methylene group directly attached to the unsaturation, said silane compound being present in either the base part (I) or the catalyst part (II) or in the base part (I) and the catalyst part (II), wherein a composition formed by combining the base part (I) and the catalyst part (II) sets at a temperature within the range of about 15 to 45° C., and wherein the unsaturated silane compound has the following structure:

$$R^2R^3C=CR^1\text{-A-SiR}_3$$

wherein

R can be different or equal and is H, a monovalent alkyl (C$_1$-C$_{22}$), aryl (C$_6$-C$_{12}$), or O—SiR$^4$$_3$ group, optionally comprising heteroatoms, with the proviso that R is not an alkoxy group or an aryloxy group, R$^1$, R$^2$, R$^3$ can be different or equal and is H, a monovalent alkyl (C$_1$-C$_{22}$), or aryl (C$_6$-C$_{12}$) group, optionally comprising heteroatoms, R$^4$ is a monovalent alkyl (C$_1$-C$_{22}$) or aryl (C$_6$-C$_{12}$) group, wherein two or three of the residues R$^4$ in O—SiR$^4$$_3$ can combine to a cyclic or polycyclic structure, A is a divalent linear, branched or cyclic hydrocarbon group (C$_1$-C$_{12}$), optionally comprising an aromatic moiety, with at least one methylene group directly attached to the unsaturation, optionally comprising O-Atoms.

17. The kit of claim 16 further comprising an inhibitor, a filler and an additive selected from modifiers, dyes, pigments, thixotropic agents, flow improvers, polymeric thickeners, surfactants, odorous substances, diluting agent(s) and/or flavorings, wherein the composition does not contain an acetylenic alcohol containing at least 6 carbon atoms, each of which may be present either in the base part (I) or the catalyst part (II) or in the base part (I) and the catalyst part (II).

18. A method of reducing the amount of hydrogen gas evolved in the reaction of an addition-curable silicone composition, said method comprising adding to the composition an unsaturated silane compound, wherein the composition sets at a temperature of about 15 to 45° C., and wherein the unsaturated silane compound has the following structure:

$$R^2R^3C=CR^1\text{-A-SiR}_3$$

wherein

R can be different or equal and is H, a monovalent alkyl (C$_1$-C$_{22}$), aryl (C$_6$-C$_{12}$), or O—SiR$^4$$_3$ group, optionally comprising heteroatoms, with the proviso that R is not an alkoxy group or an aryloxy group, R$^1$, R$^2$, R$^3$ can be different or equal and is H, a monovalent alkyl (C$_1$-C$_{22}$), or aryl (C$_6$-C$_{12}$) group, optionally comprising heteroatoms, R$^4$ is a monovalent alkyl (C$_1$-C$_{22}$) or aryl (C$_6$-C$_{12}$) group, wherein two or three of the residues R$^4$ in O—SiR$^4$$_3$ can combine to a cyclic or polycyclic structure, A is a divalent linear, branched or cyclic hydrocarbon group (C$_1$-C$_{12}$), optionally comprising an aromatic moiety, with at least one methylene group directly attached to the unsaturation, optionally comprising O-Atoms.

19. The method according to claim 18, wherein the unsaturated silane compound is present in an amount such that the hydrogen gas evolution value of said composition in 2 hours per 10.0 g of the composition is less than about 0.6 ml.

20. The method according to claim 18, wherein the amount of the unsaturated silane compound is up to about 10% by weight with respect to the cured composition.

21. The method according to claim 18, wherein the unsaturated silane compound is monofunctional.

22. The method according to claim 18, wherein the unsaturated silane compound comprises the structural element C=CH—CH$_2$ or C=C(CH$_3$)—CH$_2$.

23. The method according to claim 18, wherein the molecular weight of unsaturated silane compound is below or up to about 1000 gmol$^{-1}$.

24. A method of producing a curable composition, said method comprising the steps of:
i) providing an addition-curable siloxane compound, a siloxane crosslinker, a catalyst, and an unsaturated silane compound with at least one methylene group directly attached to the unsaturation, and
ii) mixing the components,
wherein the composition sets at a temperature of about 15 to 45° C., and wherein the unsaturated silane compound has the following structure:

$$R^2R^3C=CR^1\text{-A-SiR}_3$$

wherein

R can be different or equal and is H, a monovalent alkyl (C$_1$-C$_{22}$), aryl (C$_6$-C$_{12}$), or O—SiR$^4$$_3$ group, optionally comprising heteroatoms, with the proviso that R is not an alkoxy group or an aryloxy group, R$^1$, R$^2$, R$^3$ can be different or equal and is H, a monovalent alkyl (C$_1$-C$_{22}$), or aryl (C$_6$-C$_{12}$) group, optionally comprising heteroatoms, R$^4$ is a monovalent alkyl (C$_1$-C$_{22}$) or aryl (C$_6$-C$_{12}$) group, wherein two or three of the residues R$^4$ in O—SiR$^4$$_3$ can combine to a cyclic or polycyclic structure, A is a divalent linear, branched or cyclic hydrocarbon group (C$_1$-C$_{12}$), optionally comprising an aromatic moiety, with at least one methylene group directly attached to the unsaturation, optionally comprising O-Atoms.

25. A method of preparing a positive model, comprising the steps of:

a) providing a composition comprising:
  i) an addition-curable siloxane compound (A),
  ii) a siloxane crosslinker (B),
  iii) a catalyst (C), and
  iv) an unsaturated silane compound (D) with at least one methylene group directly attached to the unsaturation in an amount effective to reduce the amount of hydrogen gas evolved in the reaction of said composition;
wherein the composition does not contain an acetylenic alcohol containing at least 6 carbon atoms;
b) contacting the composition with a surface to obtain a negative model,
c) curing the composition, and
d) pouring the negative model after removal of the cured composition from the surface with a pouring composition to obtain a positive model.

* * * * *

UNITED STATES PATENT AND TRADEMARK OFFICE
CERTIFICATE OF CORRECTION

| | |
|---|---|
| PATENT NO. | : 7,700,712 B2 |
| APPLICATION NO. | : 10/570415 |
| DATED | : April 20, 2010 |
| INVENTOR(S) | : Joachim Zech et al. |

It is certified that error appears in the above-identified patent and that said Letters Patent is hereby corrected as shown below:

<u>Title page</u>
Item [56], References Cited, OTHER PUBLICATIONS'
Page 1, Col. 2, Line 7, delete "edition" and insert -- Edition --, therefor.
Page 1, Col. 2, Line 8, delete "tecnology" and insert -- technology --, therefor.

<u>Column 3</u>
Line 5, delete "(Hewlet" and insert -- (Hewlett --, therefor.
Line 14, delete "ml-per" and insert -- ml per --, therefor.
Lines 66-67, delete "Iso-propoxy," and insert -- Isopropoxy, --, therefor.

<u>Column 4</u>
Line 2, delete "Hepta-isopropyl" and insert -- Heptaisopropyl --, therefor.
Line 20, delete "decyclene)." and insert -- decylene). --, therefor.

<u>Column 6</u>
Line 51, delete "edition" and insert -- Edition --, therefor.

<u>Column 7</u>
Line 11, delete "consituents" and insert -- constituents --, therefor.
Line 15, delete "consituents" and insert -- constituents --, therefor.

<u>Column 8</u>
Line 29, delete "octy]," and insert -- octyl, --, therefor.
Line 37, delete "alkeny)" and insert -- alkenyl --, therefor.
Line 39, delete "allphatic" and insert -- aliphatic --, therefor.
Line 45, delete "adition" and insert -- addition --, therefor.
Line 62, delete "Karsted" and insert -- Karstedt --, therefor.

Signed and Sealed this
Twenty-eighth Day of December, 2010

David J. Kappos
*Director of the United States Patent and Trademark Office*

Column 10
Line 4, delete "moleculer" and insert -- molecular --, therefor.
Line 27, delete "hexamethyidisilazane," and insert -- hexamethyldisilazane, --, therefor.
Line 38, delete "Theological" and insert -- rheological --, therefor.

Column 14
Line 18, delete "cristoballit" and insert -- cristobalit --, therefor.
Line 33, delete "Cristoballit" and insert -- Cristobalit --, therefor.
Line 58, delete "Cristoballit" and insert -- Cristobalit --, therefor.

Column 16
Line 17, in claim 10, delete "$H_2C=CH-(CH_{24}Si(i-C_3H_7)_3$," and insert
-- $H_2C=CH-(CH_2)_4Si(i-C_3H_7)_3$, --, therefor.